United States Patent
Shirota et al.

(10) Patent No.: US 10,441,232 B2
(45) Date of Patent: Oct. 15, 2019

(54) X-RAY IMAGING APPARATUS

(71) Applicant: SHIMADZU CORPORATION, Nakagyo-Ku, Kyoto-Shi, Kyoto (JP)

(72) Inventors: Ken Shirota, Kyoto (JP); Tomoharu Okuno, Chiba (JP)

(73) Assignee: SHIMADZU CORPORATION, Kyoto (JP)

( * ) Notice: Subject to any disclaimer, the term of this patent is extended or adjusted under 35 U.S.C. 154(b) by 146 days.

(21) Appl. No.: 15/746,031

(22) PCT Filed: Jul. 22, 2015

(86) PCT No.: PCT/JP2015/070764
§ 371 (c)(1),
(2) Date: Jan. 19, 2018

(87) PCT Pub. No.: WO2017/013755
PCT Pub. Date: Jan. 26, 2017

(65) Prior Publication Data
US 2018/0214101 A1    Aug. 2, 2018

(51) Int. Cl.
*A61B 6/06* (2006.01)
*A61B 6/00* (2006.01)

(52) U.S. Cl.
CPC .............. *A61B 6/4476* (2013.01); *A61B 6/00* (2013.01); *A61B 6/06* (2013.01); *A61B 6/4429* (2013.01)

(58) Field of Classification Search
CPC ..... A61B 6/4283; A61B 6/4405; A61B 6/547; A61B 6/0492; A61B 6/4476; A61B 6/06
See application file for complete search history.

(56) References Cited

U.S. PATENT DOCUMENTS

2013/0114790 A1*  5/2013  Fabrizio .................. A61B 6/02
378/62

FOREIGN PATENT DOCUMENTS

| JP | 2003-024313 | 1/2003 |
|---|---|---|
| JP | 2004-298634 | 10/2004 |
| JP | 2006-345976 | 12/2006 |
| JP | 2008-161593 | 7/2008 |
| JP | 2011-041598 | 3/2011 |
| WO | WO 2005/065546 | 7/2005 |

OTHER PUBLICATIONS

PCT/JP2015/070764, International Search Report and Written Opinion, dated Oct. 27. 2015, 7 pages—Japanese, 2 pages—English.

* cited by examiner

*Primary Examiner* — Don K Wong
(74) *Attorney, Agent, or Firm* — Andrew F. Young, Esq.; Lackenbach Siegel, LLP

(57) ABSTRACT

An X-ray imaging apparatus is configured so that an height-position composition element 15 sends a directive to an angle driving element 44 in an imaging element 4, and the height-position compensation element 15 corrects the height-position of the X-ray tube 42 by driving of the up-and-down driving element 44 in conjunction with the imaging region that the imaging region data recognition element 14 of the console element 1, the angle of the X-ray tube 42 is corrected so that the X-ray irradiation angle of the X-ray from the X-ray tube 42 faces downward; and when the height-position compensation element 15 corrects the height-position of the X-ray tube 42 downward, the angle of the X-ray tube 42 is corrected so that the X-ray irradiation angle of the X-ray from the X-ray tube 42 faces upward.

5 Claims, 7 Drawing Sheets

FIG. 1A
FIG. 1B
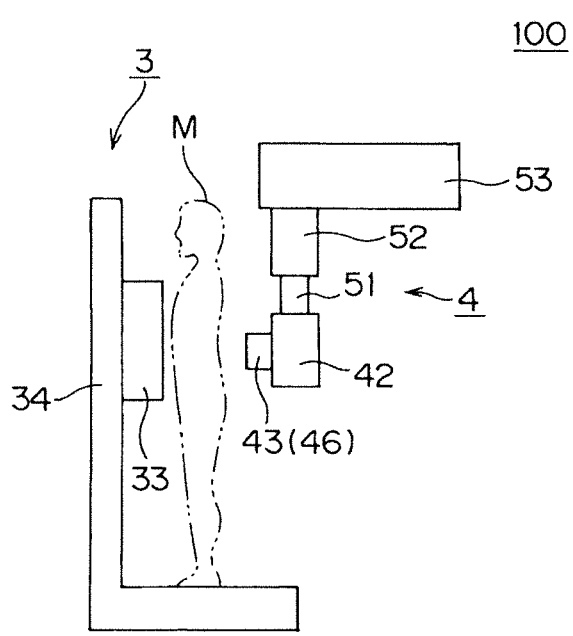
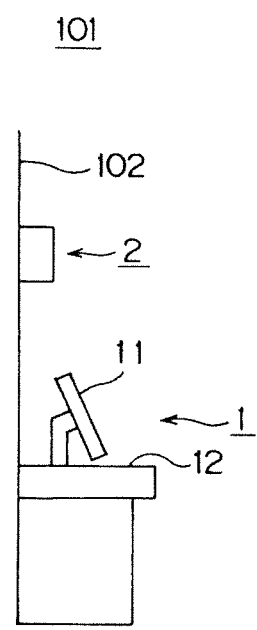

X-RAY IMAGING APPARATUS

CROSS REFERENCE TO RELATED APPLICATIONS

This application relates to, and claims priority from, PCT/JP2015/070764 filed Jul. 22, 2015 the entire contents of which are incorporated herein by reference.

FIGURE SELECTED FOR PUBLICATION

FIG. 6

BACKGROUND OF THE INVENTION

Field of the Invention

The present invention relates to an X-ray imaging apparatus that images a standing subject.

Description of the Related Art

Such an X-ray imaging apparatus comprises an X-ray tube, an X-ray detection element having the X-ray detector, such as a flat panel detector and so forth, that detects the X-ray that the X-ray tube irradiates and transmits through the upright (standing) subject, and an upright imaging stand having a lift mechanism that supports the X-ray detection element liftably. Then, the X-ray tube lifts corresponding to the height-position of the X-ray detection element and the height-position of the X-ray tube varies automatically.

The Patent Document 1 discloses an X-ray imaging apparatus in which moves manually the X-ray tube is moved manually corresponding to the imaging region. In addition, the Patent Document 2 discloses an X-ray imaging system in which an offset amount is adjusted to shift the X-ray tube to the center position relative to the imaging region when the imaging size is changed.

RELATED PRIOR ART DOCUMENTS

PATENT DOCUMENT 1: PCT International Publication WO2005/065546 A1

Patent Document 2: JP Patent Published 2006-345976 A

ASPECTS AND SUMMARY OF THE INVENTION

Objects to be Solved

When an X-ray imaging is implemented, given the X-ray tube is in place in the location at which the center of the target region of the imaging region and the focal point of the X-ray tube are facing each other, the X-ray imaging that provides the highest quality of the X-ray imaging can be implemented with no deformation in the X-ray image. For example, it is ideal that the focal point of the X-ray tube is in place at the height of thoracic vertebra of 6th to 7th (the height of an angulus inferior scapulae is equal thereto) and the X-ray is incident to a bronchial bifurcation and a proximity of a hilum of lung as the center thereof and to the X-ray detector from the vertical direction.

However, upon the actual X-ray imaging, the imaging of the necessary region is implemented by aligning the upper end of the X-ray radiation field to the height of the spinous process of 6th to 7th cervical vertebra (prominent vertebra) and setting the imaging size to be a large size (14×14 in (356 mm×356 mm)) or a half size (14 in×17 in (356 mm×432 mm)). At this time, the X-ray tube moves automatically to the position facing the center of such imaging region.

In addition, in the case of that the imaging size of the X-ray detector is smaller than the effective region, when the X-ray irradiation region is set up to match the upper end of the X-ray detector (generally called upper base); the X-ray irradiation region is set up to match the center of the X-ray detector (generally called a center base); and when the X-ray irradiation region is set up to match the lower end of the X-ray detector (generally called lower base); the X-ray tube moves automatically to the position matching the center of each X-ray irradiation region in any case.

In general, such approach does not cause any problem for the X-ray imaging, but when an accurate X-ray imaging with much less deformation is particularly implemented, an operator further manually moves the X-ray tube, which moves automatically, to the position facing the center of the target region of the imaging region to implement the X-ray imaging. However, when a large number of X-ray imagings is implemented in a day, it is too complicated for the operator to move the X-ray tube manually. In addition, it is problematic that an error may take place relative to the shift amount of the X-ray tube depending on the skill of the operator per se.

The purpose of the present invention is to solve the above objects and to provide an X-ray imaging apparatus that enables an automatic shift of an X-ray tube to the appropriate height corresponding to the imaging region.

Means for Solving the Problem

An X-ray imaging apparatus, comprising: an X-ray tube; an X-ray detection element that detects an X-ray that is irradiated from the X-ray tube and transmits through a standing subject; a standing subject imaging stand having a lifting element that supports the X-ray detection element liftably; and an X-ray tube shifting mechanism that changes a height-position of the X-ray tube corresponding to the height-position of the X-ray detection element; to a position that faces a center portion of the imaging region that the detection element detects, and further comprises: an imaging region data recognition element that acquires imaging region data relative to the subject; and a height-position compensation element that corrects the height-position of the X-ray tube in an up-and-down direction of the position that faces the center portion of the imaging region in accordance with the imaging region that the imaging region recognition element recognizes.

The X-ray imaging apparatus, wherein the X-ray apparatus adjusts a compensation amount of the height-position, which the height-position compensation element corrects, based on the height-position of the X-ray detection element.

The X-ray imaging apparatus, wherein the X-ray apparatus adjusts a compensation amount of the height-position, which the height-position compensation element corrects, based on the height data of the subject.

The X-ray imaging apparatus, further comprising: an angle compensation element that corrects an angle of the X-ray tube so that the X-ray irradiation angle of the X-ray from the X-ray tube faces downward when the height-position compensation element corrects the height-position of the X-ray tube upward, and the X-ray irradiation angle of the X-ray from the X-ray tube faces upward when the height-position compensation element corrects the height-position of the X-ray tube downward.

The X-ray imaging apparatus, further comprising: a collimator that limits the upper region of the X-ray irradiation region from the X-ray tube by a blocking member when the height-position compensation element corrects the height-position of the X-ray tube upward, and limits the lower region of the X-ray irradiation region from the X-ray tube by the blocking member when the height-position compensation element corrects the height-position of the X-ray tube downward, when the height-position compensation element corrects the height-position of the X-ray tube downward.

Effect of the Invention

An X-ray imaging apparatus, wherein the X-ray imaging apparatus corrects the height-position of the X-ray tube following a move to the position corresponding to the height-position in accordance with the imaging region so that the X-ray imaging apparatus enables an automatic move of the height-position of the X-ray tube to the appropriate height-position corresponding to the imaging region.

An X-ray imaging apparatus, wherein the height-position compensation element adjusts the compensation amount of the height-position, so that the X-ray tube can be in place in the appropriate height-position corresponding to the height of the subject.

An X-ray imaging apparatus, wherein the subject can be prevented from an exposure to an X-ray in the unnecessary X-ray irradiation region that the change of the height-position of the X-ray tube creates.

The above and other aspects, features and advantages of the present invention will become apparent from the following description read in conjunction with the accompanying drawings, in which like reference numerals designate the same elements.

BRIEF DESCRIPTION OF THE DRAWINGS

FIG. 1A, 1B are schematic views illustrating an X-ray imaging apparatus according to the aspect of the present invention.

In addition.

DETAILED DESCRIPTION OF THE PREFERRED EMBODIMENTS

Figure 2:
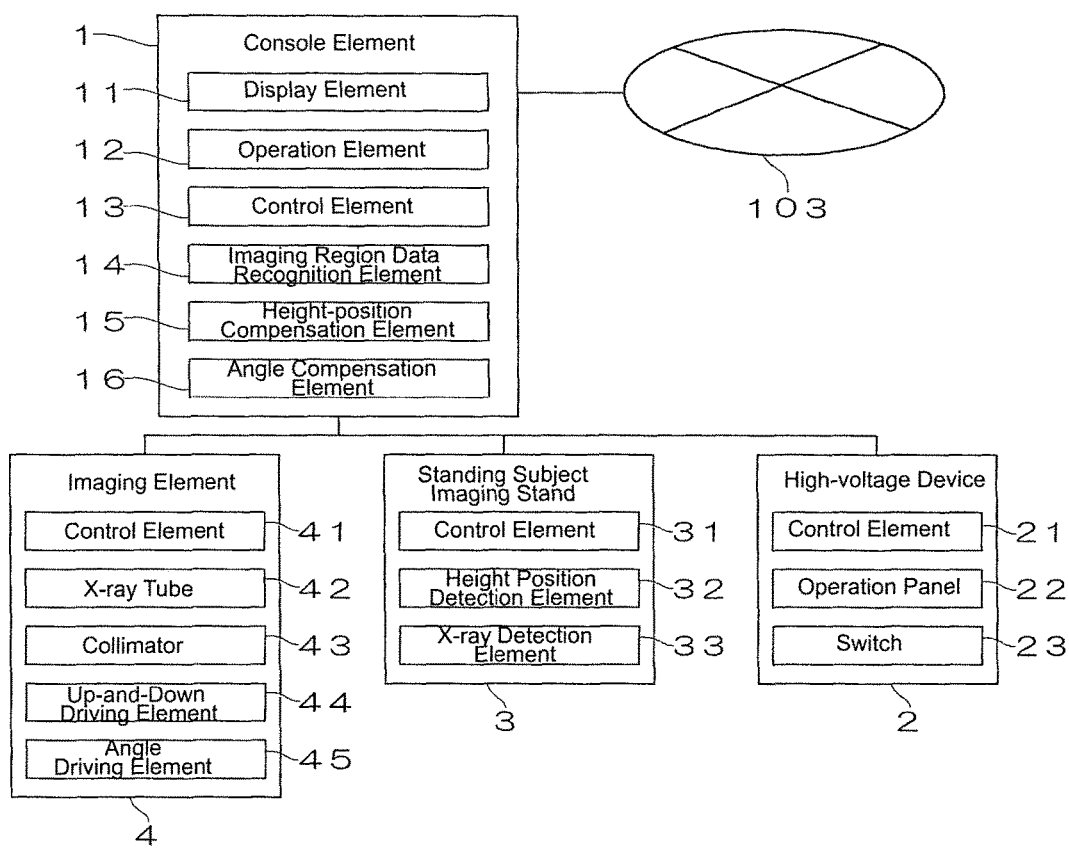
FIG. 2 is a block diagram illustrating the main control system of the X-ray imaging apparatus according to an aspect of the present invention.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

As used herein, those of skill in the art will recognize that a "computer or computational" system comprises an input device for receiving data, an output device for outputting data in any tangible form (e.g. printing or displaying on a computer screen, or in data transmission), an electronic memory for storing data as well as computer code, and a processor for executing stored computer code wherein said computer code resident in said memory will physically cause said microprocessor to read-in data via said input device, process said data within said processor and output said processed data via said output device.

It will be further understood by those of skill in the art that the apparatus and devices and the elements herein, without limitation, and including the sub components such as operational structures, circuits, communication pathways, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related X-Ray diagnostic devices, computer and operational controls and technologies of radiographic devices and all their sub components, including various circuits and combinations of circuits without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

The inventor sets forth Embodiments of the present invention based on the following FIGs. FIG. 1A, 1B are schematic views illustrating the X-ray imaging apparatus according to the aspect of the present invention. FIG. 2 is a block diagram illustrating the main control system of the X-ray imaging apparatus according to the aspect of the present invention.

The X-ray imaging apparatus according to the aspect of the present invention further comprises a console element 1 and a high-voltage device 2 that are installed in an operation room 101, in which an operator implements the X-ray imaging operation for the subject M; and a lying table 3, an upright (standing posture) imaging stand 3; and an imaging unit 4 that are installed in the imaging room 100. The imaging room 100 and the operation room 101 are separated and blocked by the partition-wall 102.

The console element 1 comprises a display element 11 including a liquid crystal display and so forth, and an operation unit 12 having a keyboard and a mouse and so forth used to execute a variety of operations. The display unit 11 displays an X-ray image. Referring to FIG. 2, the console element 1 comprises, the imaging region recognition element 14, the height-position compensation element 15 and the angle compensation element 16. Referring to FIG. 2, the control element 13 controls the console element 1. Referring to FIG. 2, the console element 1 is connected to an in-hospital local network 103 that is an in-house communication relative to the in-hospital subject management system.

The high-voltage device 2 is installed to the partition-wall 102 in the operation room 101. Referring to FIG. 2, the high-voltage device 2 comprises an operation panel 22 including the display element having a touch panel type liquid crystal display; a display panel having an input key (button) and a switch 23 that directs to start an X-ray irradiation from the X-ray tube 42. The high-voltage device 2 sets up a tube voltage of the X-ray tube 42 and a tube electric current, or an X-ray irradiation condition including such as an X-ray irradiation time length and so forth. Referring to FIG. 2, the control unit 21 controls the high-voltage unit 2.

Referring to FIG. 1A, 1B, the standing subject imaging stand 3 comprises a lifting element 34 that supports the X-ray detection element 33 liftably. The X-ray detection element 33 is called a Bucky element comprising an X-ray detector such as a flat panel detector and so forth inside thereof. On the other hand, instead of the X-ray detector such as a flat panel detector and so forth, a cassette housing the sensitizing paper and so forth can be applied. In addition, referring to FIG. 2, such standing subject imaging stand 3 comprises a height-position detection element 32 that detects the height-position of the X-ray detection element 33. Referring to FIG. 2, the control element 31 controls the standing subject imaging stand 3.

Referring to FIG. 1A, 1B, an imaging element 4 comprises: a base 53 movable in the orthogonal direction relative to the ceiling of the imaging room 100; a support column 52 extending downward from the base 53 thereof; a shifting element 51 telescopic and rotatable relative to the support column 52. The shifting element 51 supports the X-ray tube 42 and the collimator 43. Accordingly, the X-ray tube 42, and the collimator 43 are movable in a unified manner. Referring to FIG. 2, the control element 48 controls the imaging element 4. In addition, referring to FIG. 4, the imaging element 4 comprises an up-and-down driving element 44 that lifts the X-ray detection element 33 by drive-controlling a motor (not shown in FIG.), and an angle driving element 45 that changes the angles of the X-ray tube 42 and the collimator 43 by drive-controlling a motor (not shown in FIG.).

Figure 3:
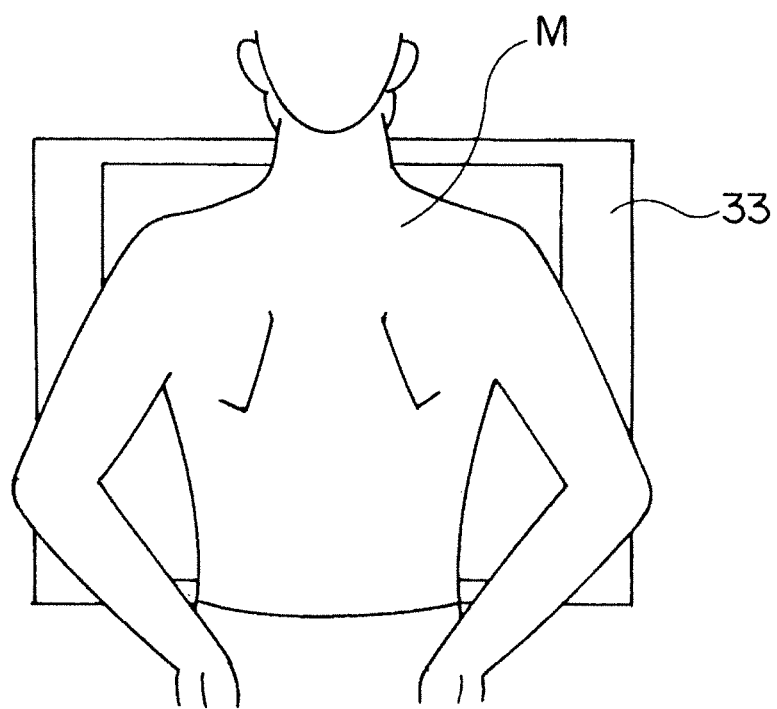
FIG. 3 is a front view, from the subject M side, illustrating an arrangement of the subject M and the X-ray detection element 33 when implementing the X-ray imaging.
Figure 4:
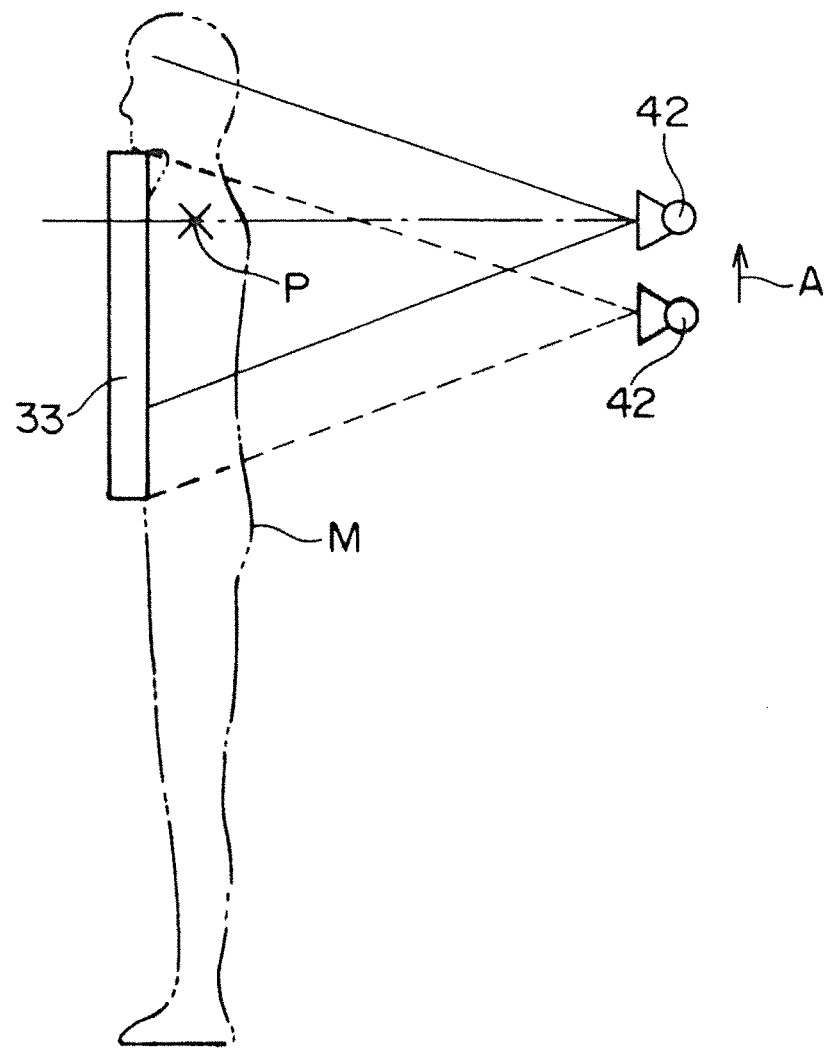
FIG. 4 is a schematic view illustrating the height-position compensation of the X-ray tube 42.
Figure 5:
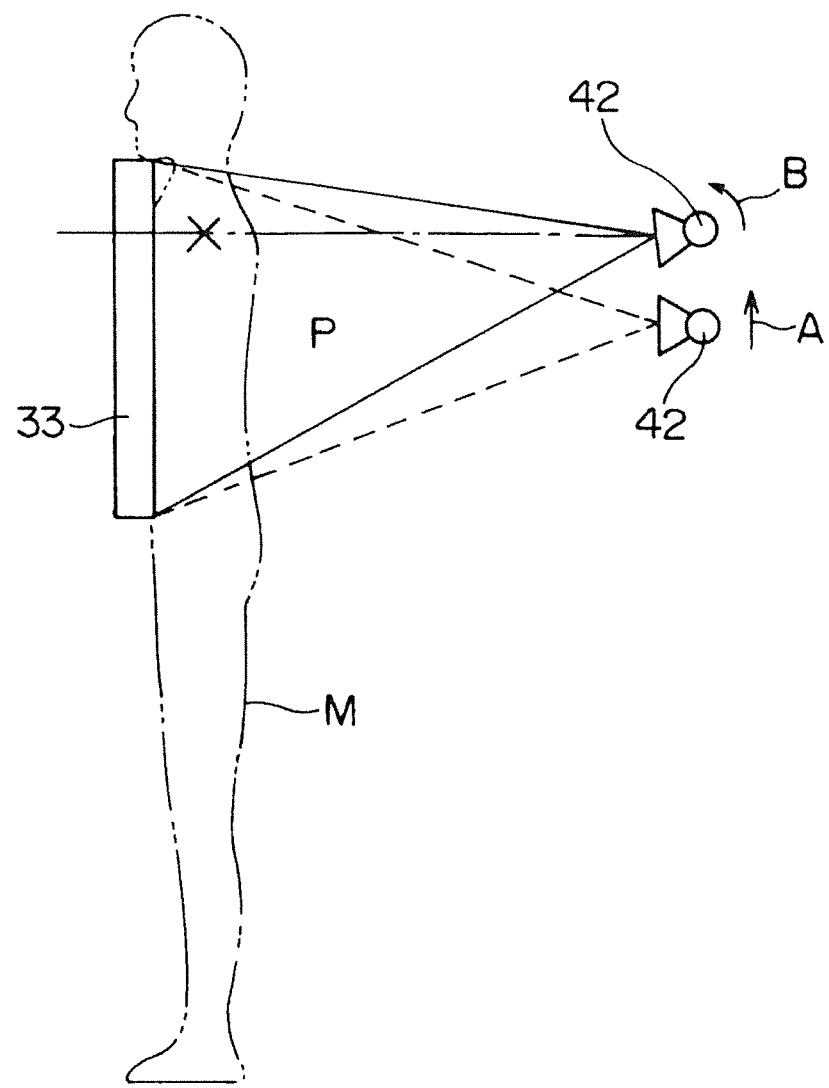
FIG. 5 is a schematic view illustrating the angle compensation of the X-ray tube 42.

Next, the inventor set forth an X-ray imaging operation with X-ray imaging apparatus having the above system. In addition, according to the aspect of the Embodiment, the case in which a chest imaging of the subject M is executed is illustrated. FIG. 3 is a front view, from the subject M side, illustrating an arrangement of the subject M and the X-ray detection element 33 when implementing the X-ray imaging. In addition, FIG. 4 is a schematic view illustrating the height-position compensation of the X-ray tube 42. In addition, FIG. 5 is a schematic view illustrating the angle compensation of the X-ray tube 42. In addition, the center of the target region relative to the imaging region is denoted as P in FIG. 4 and FIG. 5. In addition, the collimator 43 and so forth are not shown in FIG. 4 and FIG. 5.

When the imaging begins, the examination order relative to the subject M (patient data and the imaging region) is transferred via the in-hospital local area network 103 and the imaging condition using is retrieved using the anatomical program and so forth. In addition, the selected imaging region is sent out to the imaging region data recognition element 14 in the console element 1 and stored in the memory.

In addition, in parallel, the subject M is erected in front of the X-ray detection element 33 of the standing subject imaging stand 3. Then, the operator adjusts manually the height-position of the X-ray detection element 33. At this time, referring to FIG. 3, the X-ray detection element 33 is lifted up until the contact position at which the chin of the subject M contacts the upper end of the X-ray detection element 33. Under such condition, the upper end of the X-ray irradiation field is the height-position of the 6th-7th spinous process of cervical vertebra (prominent vertebra) of the subject M. Then, the height-position of the detection element 33 at this time is detected by the height-position detection element 32 referring to FIG. 2 and the height-position data thereof is sent out to the console element 1.

When such height-position of the X-ray detection element 33 is determined, the X-ray tube 42 and the collimator 43 are in place facing the X-ray detection element 33 in conjunction with the base 53 of the imaging element 4, the support element 52 and the moving element 51. Then, the X-ray tube 42 and the collimator 43 lift by driving of the up-and-down driving element 44 and the X-ray tube 42 and the collimator 43 are positioned based on the height-position of the X-ray detection element 33 and the irradiation field size thereat.

Referring to FIG. 4, the X-ray irradiated from the X-ray tube 42 positioned in such way to the subject M is indicated by the broken line. Even under such condition, the center P of the target region relative to the imaging region of the subject M is possibly imaged. However, under such condition, the center P of the target region relative to the imaging region and the height-position of the X-ray tube 42 are different to each other, so that an X-ray is irradiated from the diagonal direction relative to the center P of the target region and the X-ray image is deformed.

Accordingly, relative to the X-ray imaging apparatus according to the present invention, the height-position compensation element 15 sends out the directive to the up-and-down driving element 44 of the imaging element 4 in conjunction with the imaging region recognized by the imaging region data recognition element 14 in the console element 1, and corrects the height-position of the X-ray tube 42 by the up-and-down driving element 44. In such case, for example, when implementing the chest imaging, the height-position of the X-ray tube 42 is 9 cm higher, and when implementing the abdomen imaging, the height-position of the X-ray tube 42 is 3 cm lower.

Referring to FIG. 4, as indicated by the arrow A, the X-ray irradiated from the X-ray tube 42 of which height-position is corrected to be 9 cm higher for the chest imaging to the subject M is indicated by the solid line. Under such condition, the center P of the target region relative to the imaging region and the height-position of the X-ray tube 42 are approximately identical to each other, so that an X-ray is irradiated from the vertical direction relative to the center P of the target region and the X-ray image is not deformed at all.

In addition, when the height-position of the X-ray tube 42 is corrected in such way, the compensation amount (9 cm) of the height-position is preferably adjusted corresponding to the height of the subject M. When the subject M is tall, the center P of the target region is in place at the higher position than the center P of the target region of the imaging region that is expected from the height-position of the X-ray detection element 33, so that it is deemed that the center P of the target region P and the X-ray tube 42 are in place facing more accurately with each other by increasing the compensation amount of the height-position much more.

According to one aspect of the Embodiment, when the compensation amount of the height-position is adjusted in such way, the height-position compensation element 15 of the console element 1 adjusts the compensation amount of the height-position based on the height-position of the X-ray detection element 33 detected by the height-position detection element 32 of the standing subject imaging stand 3. The reason is that the height-position of the X-ray detection element 33 on the X-ray imaging is proportional to the height of the subject M.

In addition, according to the aspect of the alternative Embodiment, when the compensation amount of the height-position is adjusted in such way, the height-position compensation element 15 of the console element 1 adjusts the compensation amount of the height-position based on the height data of the subject M of the patient data of the subject M transferred via the in-hospital network 103.

Accordingly, when the height-position of the X-ray tube 42 is corrected, the center P of the target region relative to the imaging region and the height-position of the X-ray tube 42 are identical to each other, so that an X-ray is irradiated from the vertical direction relative to the center P of the target region and the accurate X-ray image can be obtained. However, referring to FIG. 4, the X-ray that is not incident into the X-ray detection element 33 is irradiated from the X-ray tube 42 to the subject M, so that the subject M is exposed to unnecessary X-ray.

Accordingly, with regard to the X-ray imaging apparatus according to the aspect of the present invention, when the angle compensation element 16 of the console element 1 sends the directive to the angle driving element 45 in the imaging element 4, and the height-position compensation element 15 corrects the height-position of the X-ray tube 42 upward by the angle driving element 45, the angle of the X-ray tube is corrected so that the X-ray irradiation angle of the X-ray from the X-ray tube 42 faces downward; and when the height-position compensation element 15 corrects the height-position of the X-ray tube 42 downward, the angle of the X-ray tube 42 is corrected so that the X-ray irradiation angle of the X-ray from the X-ray tube 42 faces upward.

FIG. 5 is a schematic view illustrating such angle compensation operation of the X-ray tube 42. Referring to FIG. 5, with regard to the X-ray imaging apparatus according to the aspect of the present invention, when the height-position compensation element 15 directs the X-ray tube 42 to lift the height thereof as indicated by the arrow A, the angle of the X-ray tube 42 is changed so that the irradiation angle of the X-ray from the X-ray tube 42 faces downward as indicated by the arrow B. Accordingly, the subject M can be prevented from an unnecessary X-ray exposure. Even in such case, the center P of the target region relative to the imaging region and the height-position of the X-ray tube 42 are identical each other, so that an X-ray is irradiated from the vertical direction relative to the center P of the target region and the X-ray image is not deformed at all, accordingly.

In addition, when the height-position compensation element 15 directs the X-ray tube 42 to down the height thereof, the angle of the X-ray tube 42 is changed so that the irradiation angle of the X-ray from the X-ray tube 42 faces upward.

Figure 6:
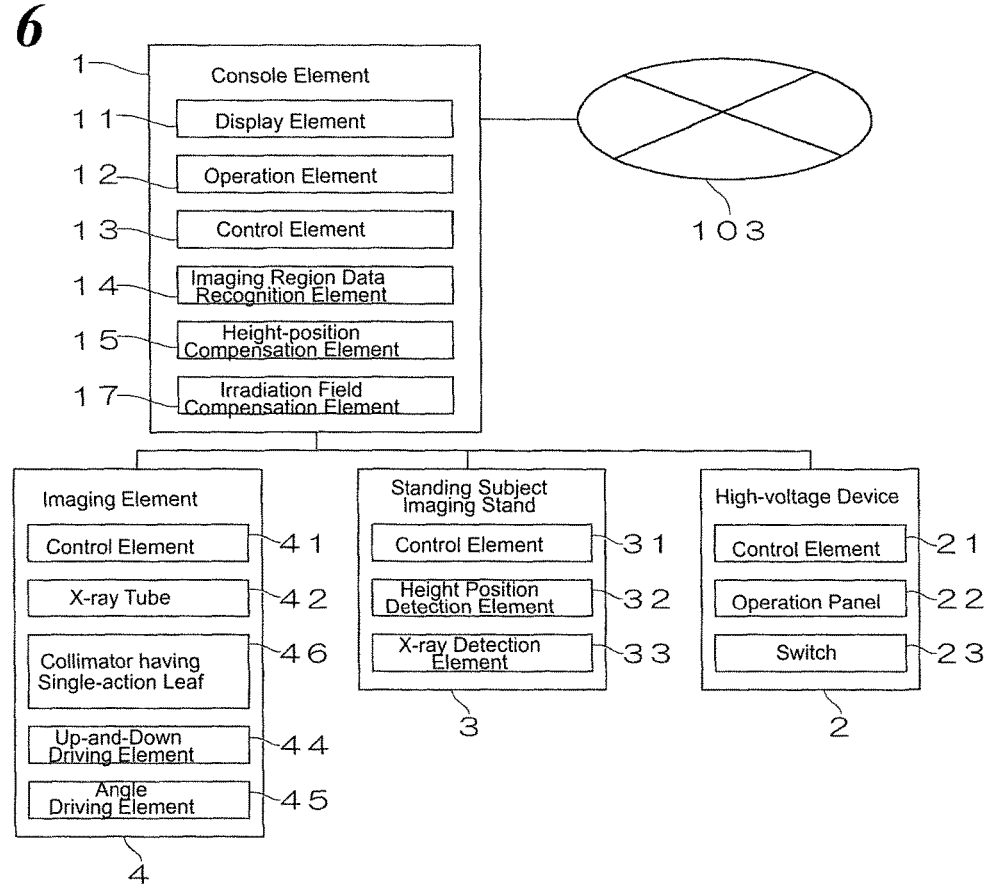
FIG. 6 is a block diagram illustrating the main control system of the X-ray imaging apparatus according to an aspect of the Embodiment 2 of the present invention.
Figure 7:
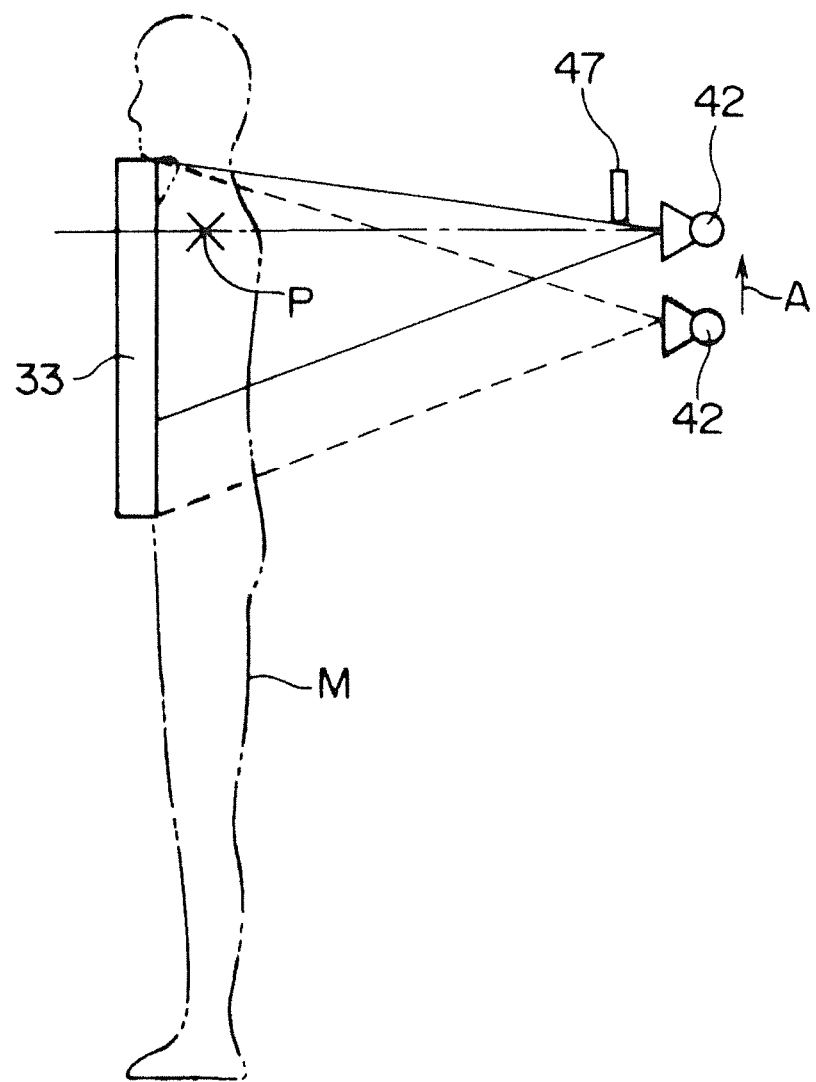
FIG. 7 is a schematic view illustrating the compensation operation of the irradiation field.

Next, the inventor sets forth the other Embodiment of the present invention. FIG. 6 is a block diagram illustrating the main control system of the X-ray imaging apparatus according to an aspect of the Embodiment 2 of the present invention. FIG. 7 is a schematic view illustrating the compensation operation of the irradiation field. In addition, the same member as illustrated according to the aspect of the Embodiment 1 set forth above is not set forth while providing the identical reference sign.

With regard to the X-ray imaging apparatus according to the aspect of the Embodiment 1, the angle of the X-ray tube 42 is corrected, so that the subject M is prevented from unnecessary X-ray exposure. With regard to the X-ray imaging apparatus according to the aspect of the Embodiment 2, a single-acting leaf 47 is applied to the blocking member, so that the subject M is prevented from unnecessary X-ray exposure.

With regard to the X-ray imaging apparatus according to the aspect of the Embodiment 2, referring to FIG. 6, an irradiation field compensation element 17 is adopted instead of the angle compensation element 16 of the console element 1 according to the aspect of the Embodiment 1, the collimator 46 having the single-action leaf is adopted instead of the collimator 43 of the imaging element 4 according to the aspect of the Embodiment 1. In addition, for example, as disclosed in the Patent Document JP2014-083413 A, the collimator 46 having the single-action leaf is the collimator having the single-action collimator that is squeezable only one side relative to the X-ray irradiation field in addition to the 4 normal collimator leaves.

Referring to FIG. 4, with regard to the X-ray imaging apparatus according to the aspect of the Embodiment 2, the X-ray that is not incident into the X-ray detection element 33 is irradiated from the X-ray tube 42 to the subject M, so that the single-action leaf 47 referring to FIG. 7 is applied to prevent that the subject M is exposed to unnecessary X-ray. Specifically, with regard to the X-ray imaging apparatus according to the aspect of the Embodiment 2 of the present invention, when the irradiation field compensation element 17 of the console element 1 sends the directive to the collimator 46 having the single-action leaf relative to the imaging element 4; and the height-position compensation element 15 corrects the height-position of the X-ray tube 42 upward by the angle driving element 45, the single-action leaf 47 restricts the upper region of the X-ray irradiation region from the X-ray tube 42; and the height-position compensation element 15 corrects the height-position of the X-ray tube 42 downward, the single-action leaf 47 restricts the lower region of the X-ray irradiation region from the X-ray tube 42.

Specifically, referring to FIG. 7, with regard to the X-ray imaging apparatus according to the aspect of the Embodiment 2 of the present invention, when the height-position compensation element 15 directs the X-ray tube 42 to lift the height thereof as indicated by the arrow A, the single-action leaf 47 restricts the upper region of the X-ray irradiation region from the X-ray tube 42. Accordingly, the subject M can be prevented from an unnecessary X-ray exposure. Even in such case, the center P of the target region relative to the imaging region and the height-position of the X-ray tube 42 are identical to each other, so that an X-ray is irradiated from the vertical direction relative to the center P of the target region and the X-ray image is not deformed at all, accordingly.

In addition, when the height-position compensation element 15 directs the X-ray tube 42 to down the height thereof, the single-action leaf 47 restricts the lower region of the X-ray irradiation region from the X-ray tube 42.

According to the aspect of the Embodiment, the inventor sets forth the chest imaging, but the present invention is not limited thereto. For example, given under the normal positional relationship, on a foot-toe imaging, the target region is incorporated in the lower side of the X-ray irradiation region and the X-ray is incident into the foot-toe, as the target region, from the diagonal direction. Accordingly, the position of the X-ray tube bulb is offset and corrected against the foot-toe and further, the angle of the X-ray tube 42 or the single-action leaf 47 adjusts the size of the irradiation region, so that the X-ray image relative to the target region can be imaged with no deformation at all. In addition, when the center of the normal image range and the center of the standard target region relative to the imaging target region are shifted each other, a variety of aspects of Embodiments can be achieved as long as controlling that the center of the standard target region matches the focal point of the X-ray.

Those of skill would further appreciate that the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

The various illustrative logical blocks, modules, and circuits described in connection with the embodiments disclosed herein, may be implemented or performed with a general or specific purpose processor, or with hardware that carries out these functions, e.g., a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general-purpose processor may be a microprocessor, and in the alternative, the processor may be any conventional processor, controller, microcontroller, or state machine. The processor can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as a RF link running under a wireless protocol such as 802.11. Likewise, an external bus may be any of but not limited to hard wired external busses such as IEEE-1394 or USB. The computer system can also have a user interface port that communicates with a user interface, and which receives commands entered by a user, and a video output that produces its output via any kind of video output format, e.g., VGA, DVI, HDMI, display port, or any other form. This may include laptop or desktop computers, and may also include portable computers, including cell phones, tablets such as the IPAD™ and Android™ platform tablet, and all other kinds of computers and computing platforms.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, using cloud computing, or in combinations. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

Operations as described herein can be carried out on or over a web site. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

REFERENCE OF SIGNS

1 Console element
2 High-voltage device
3 Standing subject imaging stand
4 Imaging element
14 Imaging region recognition element
15 Height-position compensation element
16 Angle compensation element
17 Irradiation field compensation element
32 Height-position detection element
33 X-ray detection element
42 X-ray tube
43 Collimator
44 Up-and-down driving element
45 Angle driving element
46 Collimator having the single-action leaf
103 In-hospital network
M Subject
P Center of the target region

What is claimed is:

1. An X-ray imaging apparatus, comprising:
    an X-ray tube;
    an X-ray detection element that detects an X-ray that is irradiated from said X-ray tube and transmits through a standing subject;
    a standing subject imaging stand having a lifting element that supports said X-ray detection element liftably; and
    an X-ray tube shifting mechanism that changes a height-position of said X-ray tube corresponding to a height-position of said X-ray detection element to a position that faces a center portion of the imaging region that said detection element detects; and
    further comprising:
        an imaging region data recognition element that acquires imaging region data relative to said subject; and
        a height-position compensation element that corrects the height-position of said X-ray tube in an up-and-down direction of the position facing the center portion of the imaging region in accordance with an imaging region that said imaging region recognition element recognizes.

2. The X-ray imaging apparatus, according to claim 1, wherein:
    said height-position compensation element adjusts a compensation amount of the height-position based on the height-position of said X-ray detection element.

3. The X-ray imaging apparatus, according to claim 1, wherein:
    said height-position compensation element adjusts a compensation amount of the height-position based on the height data of said subject.

4. The X-ray imaging apparatus, according to claim 1, further comprising:
    an angle compensation element that corrects an angle of said X-ray tube so that the X-ray irradiation angle of the X-ray from said X-ray tube faces downward when said height-position compensation element corrects the height-position of said X-ray tube upward; and the X-ray irradiation angle of the X-ray from said X-ray tube faces upward when said height-position compensation element corrects the height-position of the X-ray tube downward.

5. The X-ray imaging apparatus, according to claim 1, further comprising:
    a collimator that limits the upper region of the X-ray irradiation region from said X-ray tube by a blocking member when said height-position compensation element corrects the height-position of said X-ray tube upward, and limits the lower region of the X-ray irradiation region from the X-ray tube by the blocking member when the height-position compensation element corrects the height-position of said X-ray tube downward, when the height-position compensation element corrects the height-position of said X-ray tube downward.

* * * * *